United States Patent [19]

Nishio et al.

[11] Patent Number: 4,741,816
[45] Date of Patent: May 3, 1988

[54] OXYGEN SENSOR

[75] Inventors: Hisaharu Nishio, Tokai; Toshio Okumura, Kakamigahara, both of Japan

[73] Assignee: NGK Spark Plug Co., Ltd., Aichi, Japan

[21] Appl. No.: 948,467

[22] Filed: Dec. 29, 1986

Related U.S. Application Data

[63] Continuation of Ser. No. 824,941, Feb. 3, 1986, abandoned, which is a continuation of Ser. No. 662,690, Oct. 19, 1984, abandoned.

[30] Foreign Application Priority Data

Nov. 10, 1983 [JP] Japan .............................. 58-174005[U]
Nov. 11, 1983 [JP] Japan .............................. 58-175033[U]

[51] Int. Cl.⁴ .............................................. G01N 27/58
[52] U.S. Cl. .................................. 204/425; 204/408; 204/424
[58] Field of Search ............... 204/408, 424, 425, 426, 204/427, 428; 339/252 P

[56] References Cited

U.S. PATENT DOCUMENTS

| | | | |
|---|---|---|---|
| 3,394,341 | 7/1968 | Venn .............................. | 339/252 P |
| 3,693,140 | 9/1972 | Nijman .......................... | 339/252 P |
| 4,057,477 | 11/1977 | Weyl et al. ................. | 204/408 X |
| 4,141,813 | 2/1979 | Kita et al. ................... | 204/428 |
| 4,145,272 | 3/1979 | Nakamura et al. ......... | 204/428 X |
| 4,175,019 | 11/1979 | Murphy ........................ | 204/429 |
| 4,187,163 | 2/1980 | Steinke et al. ............. | 204/428 |
| 4,212,720 | 7/1980 | Maurer et al. ............. | 204/424 |
| 4,328,295 | 5/1982 | Tanaka et al. ............. | 204/424 X |
| 4,370,213 | 1/1983 | Oki ............................... | 204/426 |
| 4,402,820 | 9/1983 | Sano et al. .................. | 204/429 X |
| 4,437,971 | 3/1984 | Csanitz et al. ............. | 204/428 X |
| 4,507,191 | 3/1985 | Ebizawa et al. ............ | 204/427 |

FOREIGN PATENT DOCUMENTS

| | | | |
|---|---|---|---|
| 0056837 | 8/1982 | European Pat. Off. ........... | 204/428 |
| 2811066 | 9/1979 | Fed. Rep. of Germany . | |
| 3041581 | 10/1981 | Fed. Rep. of Germany . | |
| 3105089 | 1/1982 | Fed. Rep. of Germany . | |
| 2396292 | 1/1979 | France . | |
| 1523010 | 8/1978 | United Kingdom . | |

*Primary Examiner*—John F. Niebling
*Assistant Examiner*—Nam X. Nguyen
*Attorney, Agent, or Firm*—Oblon, Fisher, Spivak, McClelland & Maier

[57] ABSTRACT

An oxygen sensor including an oxygen sensing element having one closed end and inner and outer electrode layers formed on the inner and outer surfaces thereof, an output withdrawing lead wire electrically connected to the inner electrode layer formed on the inner surface of the oxygen sensing element, and a metallic terminal disposed in connection between the output withdrawing lead wire and the inner electrode layer. The metallic terminal includes opposed resilient portions separated by a gap and disposed in contact with the inner periphery of the inner electrode layer to apply a radial force to the inner electrode layer, whereby not only the damage of the oxygen sensing element is prevented but also the mounting operation can be done easily without threaded insertion of the metallic terminal.

26 Claims, 6 Drawing Sheets

 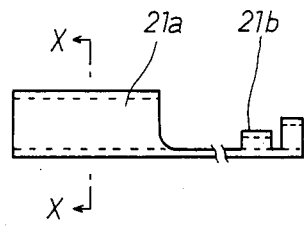 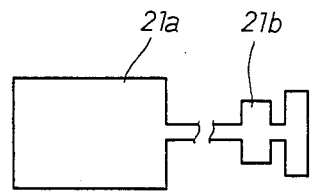
Fig. 3C　　　Fig. 3B　　　Fig. 3A
 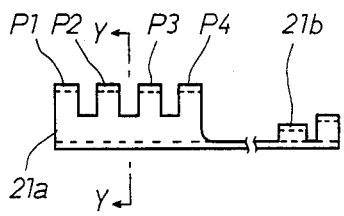 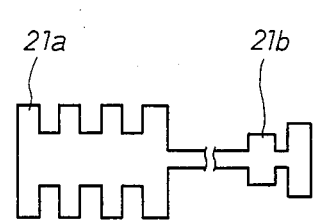
Fig. 4C　　　Fig. 4B　　　Fig. 4A
 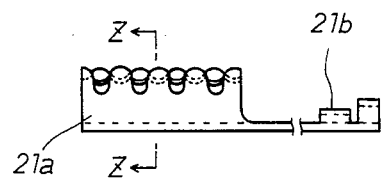 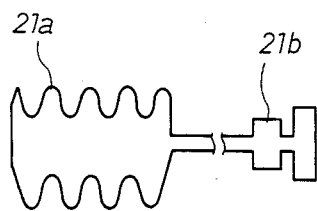
Fig. 5C　　　Fig. 5B　　　Fig. 5A

OXYGEN SENSOR

This application is a continuation of abandoned application Ser. No. 824,941, filed Feb. 3, 1986, which is a continuation of abandoned parent application Ser. No. 662,690, filed Oct. 19, 1984.

BACKGROUND OF THE INVENTION (1) Field of the Invention

The present invention relates to a structure of an oxygen sensor for detecting the concentration of oxygen in the exhaust gases from various combustion apparatus.

The present invention is also concerned with a structure of an oxygen sensor equipped with a heater for heating an oxygen sensing element.

(2) Description of the Prior Art

Oxygen sensors using an oxygen sensing element comprising a solid electrolyte such as zirconia have heretofore been widely used for detecting the concentration of oxygen in the exhaust gases from various combustion apparatus including internal combustion engines.

Oxygen sensors of this type, as shown in FIG. 1, are composed of a cylindrical oxygen sensing element 1 formed of zirconia or the like and having one closed end, inner and outer electrode layers 2 and 3 formed of platinum or the like deposited on the inner and outer surfaces of the oxygen sensing element 1, an output withdrawing lead wire 4 connected electrically to the inner electrode layer 2 for withdrawing output from the same layer, and a housing 5 for holding the oxygen sensing element 1, the housing 5 being connected electrically to the outer electrode layer 3, in which the inner and outer electrode layers 2 and 3 are contacted with ambient air and exhaust gases, respectively, whereby the concentration of oxygen in the exhaust gases is sensed.

Thus, it is necessary that the inner electrode layer 2 be contacted with ambient air and at the same time connected to the output withdrawing lead wire 4. But, various difficulties have therefore been encountered in the connection between the output withdrawing lead wire 4 and the inner electrode layer 4. For example, an internal thread portion 6 is formed in the inner surface of an open end portion of the oxygen sensing element 1, and a tubular metallic terminal 8 having an external thread portion 7 is engaged with the internal thread portion 6 and at the same time connected to the output withdrawing lead wire 4, or a coil-like terminal is engaged with the internal thread portion and at the same time connected to the output withdrawing lead wire, to thereby electrically connect the inner electrode layer 2 and the output withdrawing lead wire 4 with each other. In these cases, however, a large clamping stress may be exerted on the internal thread portion 6 thereby causing damage of the oxygen sensing element 1. It has also been tried to prevent damage of the oxygen sensing element by using a coiled spring terminal in place of the cylindrical metallic terminal 8 and fitting it threadedly in the internal thread portion 6. But, in this case, since the outside diameter of the coiled spring terminal is formed larger than the inside diameter of the internal thread portion 6 so as to press the inner periphery of the internal thread portion 6, it is not easy to bring the coiled spring terminal into engagement with the internal thread portion 6, the operation being troublesome.

Further, in view of the characteristic of the oxygen sensing element that this sensing element is improved in its oxygen sensing performance while it is held at a predetermined temperature, there has been proposed an oxygen sensor incorporating a heater for heating the oxygen sensing element. In this case, however, it is necessary to dispose such heater in the interior of the oxygen sensing element, that is, inside the inner electrode layer, so particularly in the case of using a rod-like ceramic heater as such heater, a problem is encountered in the fixing method for the heater body. And in the case of using a coil-like terminal, there will not occur breakage of the oxygen sensing element because a clamping stress is not applied thereto, but it is not easy and is troublesome to fit such terminal threadedly in the internal thread portion.

Moreover, the heater is fixed using an adhesive or the like to heat the oxygen sensing element. But, in this case, the heater cannot be fixed firmly due to a change of the adhesive or the like with the lapse of time caused by heating or vibration, thus resulting in damage of the inner electrode layer or the heater itself.

SUMMARY OF THE INVENTION

It is an object of the present invention to provide an oxygen sensor which permits an easy connection of an output withdrawing lead wire to an inner electrode layer without forming any thread portion thereby eliminating the development of a clamping stress and preventing damage of an oxygen sensing element.

It is another object of the present invention to provide an oxygen sensor in which the connection of an output withdrawing lead wire to an inner electrode layer is ensured without being influenced by thermal expansion and contraction or vibration thereby ensuring withdrawal of output from the inner electrode layer.

It is a further object of the present invention to provide an oxygen sensor in which an output withdrawing lead wire is connected firmly to an inner electrode wire without the need of forming a thread portion in the latter thereby ensuring withdrawal of output from the inner electrode layer and whereby the mounting operation can be done easily and the damage of an oxygen sensing element caused by a clamping stress can be prevented.

It is still a further object of the present invention to provide an oxygen sensor in which a heater is fixed firmly in the interior of an oxygen sensing element without the need of using an adhesive or the like and therefore the damage or breakage of the heater and an inner electrode layer caused by heat or vibration can be prevented.

In order to attain the above-mentioned objects, the present invention provides according to one aspect thereof an oxygen sensor including a cylindrical oxygen sensing element having one closed end and also having inner and outer element having one closed end and also having inner and outer electrode layers formed on the inner and outer surfaces thereof, and an output withdrawing lead wire connected electrically to the inner electrode layer formed on the inner surface of the oxygen sensing element, characterized in that a metallic terminal which urges the inner periphery of the inner electrode layer in a radial direction from the interior is used in the connection between the output withdrawing lead wire and the inner electrode layer.

According to another aspect of the present invention for achieving the foregoing objects, there is provided an oxygen sensor including a cylindrical oxygen sensing element having one closed end and also having inner and outer electrode layers formed on the inner and outer surfaces thereof, a heater for maintaining the oxygen sensing element at a predetermined temperature and an output withdrawing lead wire connected electrically to the inner electrode layer formed on the inner surface of the oxygen sensing element, characterized in that a metallic terminal adapted to be held in place while urging the inner periphery of the inner electrode layer in a radial direction from the interior is used for connection between the output withdrawing lead wire and the inner electrode layer.

BRIEF DESCRIPTION OF THE DRAWINGS

FIG. 3 illustrates a shape of a connecting portion 21a of a metallic terminal 21, in which A is a development view, B is a side view and C is a sectional view taken on line X—X;

FIGS. 4 and 5 illustrate other shapes of metallic terminals 21 in each of which, like FIG. 3, A is a development view, B is a side view and C is a sectional view taken on line Y—Y or Z—Z;

DESCRIPTION OF PREFERRED EMBODIMENTS

Figure 1:
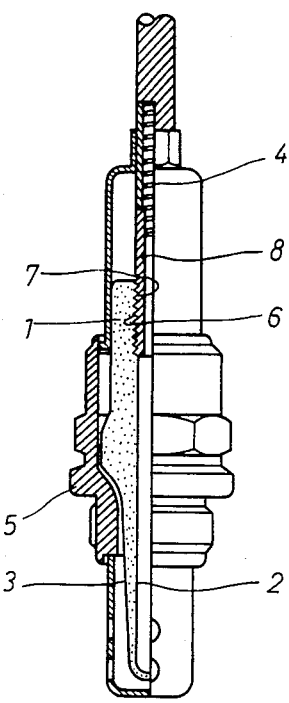
FIG. 1 is a semi-sectional front view showing an example of a conventional oxygen sensor.
Figure 2:
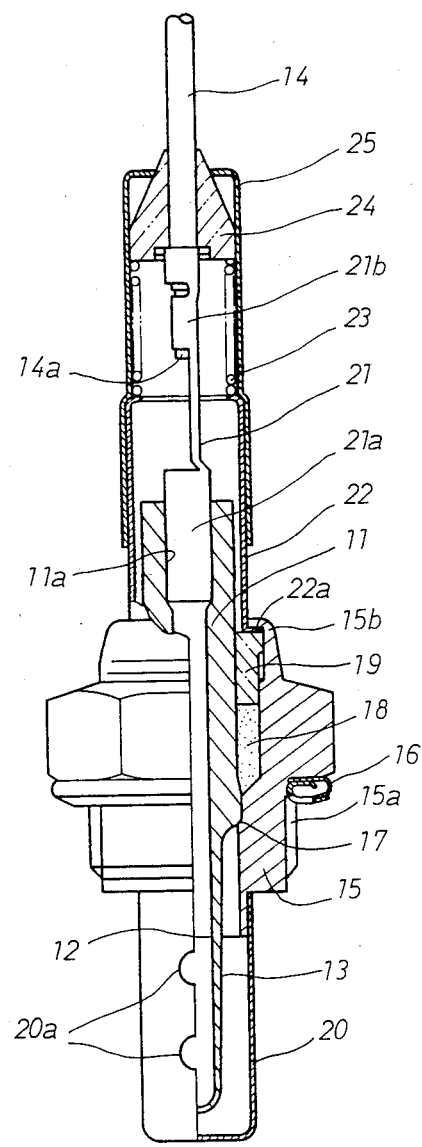
FIG. 2 is a partially cut-away front view of an oxygen sensor according to a first embodiment of the present invention.

Embodiments of the present invention will be described below with reference to the drawings FIG. 2 is a partially cut-away front view of an oxygen sensor according to a first embodiment of the present invention, in which the reference numeral 11 denotes an oxygen sensing element having one closed end and cylindrically formed of a solid electrolyte such as zirconia; the numeral 12 denotes an inner electrode layer of platinum deposited on the inner surface of the oxygen sensing element 11 by vacuum evaporation or other suitable method; the numeral 13 denotes an outer electrode layer formed on the outer surface of the oxygen sensing element 11 like the inner electrode layer 12; the numeral 14 denotes an output withdrawing lead wire connected electrically to the inner electrode layer 12 for withdrawing output from the latter; and the numeral 15 denotes a cylindrical housing for holding the oxygen sensing element 11, the housing 15 being electrically connected to the outer electrode layer 13. On the outer periphery of the housing 15 is formed a thread portion 15a for mounting the oxygen sensor to a combustion apparatus, and a gasket 16 for preventing a leakage of exhaust gases is provided on the portion of the housing to be brought into abutment with the wall surface of the combustion apparatus. Further, the housing 15 is formed with a caulking portion 15b, and by caulking this caulking portion 15b the oxygen sensing element 11 is held by the housing 15 through plate packing 17, talc 18, caulking ring 19 and tubular shell flange portion 22a which are disposed on the inner periphery of the housing 15. The numeral 20 denotes a protector for protecting the oxygen sensing element 11. The protector 20, which is attached to a combustion apparatus-side fore end portion 15c of the housing 15, has a plurality of exhaust gas passing holes 20a so that exhaust gases may be brought into contact with the outer electrode layer 13.

The numeral 21 denotes a metallic terminal for connecting the inner electrode layer 12 of the oxygen sensing element 11 with the output withdrawing lead wire 14. The metallic terminal 21 is formed using a spring steel sheet which in this embodiment is stainless steel strip for spring SUS631-CSP, a precipitation hardening type stainless steel, and has a connecting portion 21a formed by rounding such spring steel sheet so as to exhibit a resilient force in a radial direction as will be described later. The connecting portion 21a is inserted under compressive force into an opening 11a of the oxygen sensing element and then released, whereby it is fixed in pressure contact and electrical connection with the inner electrode layer 12 formed on the inner surface of the opening. The connecting portion 21a is protected by a tubular shell 22 having a flange 22a. The metallic terminal 21 and the output withdrawing lead wire 14 are connected by pressure bonding at the respective terminal portion 21b and core 14a, and are protected by a protective sleeve 25 which prevents ingress of water or oil into the interior of the sensor. The protective sleeve 25 has a spring 23 and a seal member 24 which is fixed to an end portion of the protective sleeve by the spring 23 and through which is inserted the lead wire and at the same time the lead wire is held by the protective sleeve.

The metallic terminal 21, which is a principal portion in the present invention, has such a shape as shown in FIG. 3. As is apparent from the development view of FIG. 3A, the metallic terminal 21 is formed by punching a metallic sheet and it is provided with the connecting portion 21a and the terminal portion 21b which is a solderless terminal provided at an end of an elongated extension extending from the connecting portion 21a. The connecting portion 21a is formed merely cylindrically from a rectangular metallic sheet, having no thread portion, and thus can be easily formed. Therefore, in the case of using the metallic terminal 21, it is not necessary to form a thread portion in the inner periphery of the opening portion of the oxygen sensing element 11, and its mounting operation can be done easily. In FIG. 3, A is a side view of the inner electrode connecting portion 21a and C is a sectional view taken on line X—X.

FIGS. 4 and 5 illustrate different shapes of connecting portions 21a. The connecting portion 21a shown in FIG. 4 is obtained by forming rectangular notches in a rectangular metallic sheet and then rounding the sheet cylindrically, while the connecting portion 21a shown in FIG. 5 is obtained by forming wavy notches in a rectangular metallic sheet and then rounding the sheet cylindrically. Thus, in the case of forming the metallic terminal by notching a rectangular metallic sheet, the metallic terminal comes to have a plurality of pressing portions against the inner electrode layer. Therefore, for example, even in the event the metallic terminal is deformed by an external force and a pressing portion P1 shown in FIG. 4 loses its resilience, the metallic terminal is firmly fixed to the inner electrode layer by the resilience of other pressing portions P2 to P4, thereby ensuring withdrawal of the output from the metallic terminal.

Although in the above embodiment the connection between the metallic terminal and the lead wire is effected by pressure bonding of the metallic terminal, there may be adopted any other conventional bonding method, e.g. soldering.

Figure 6:
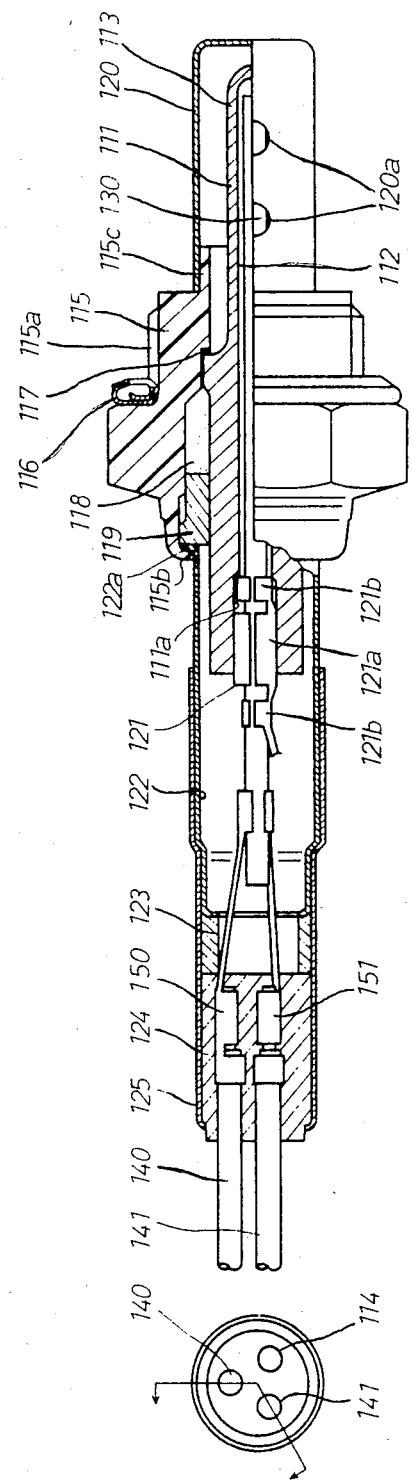
FIG. 6 illustrates an oxygen sensor according to a second embodiment of the present invention, in which A is a partially cut-away front view and B is a left side view.

Referring now to FIG. 6, there is illustrated an oxygen sensor according to a second embodiment of the present invention, in which A is a partially cut-away front view and B is a left side view. In FIG. 6, the numeral 111 denotes an oxygen sensing element cylindrically formed of a solid electrolyte such as zirconia and having one closed end; the numeral 112 denotes an inner electrode layer of platinum deposited on the inner surface of the oxygen sensing element 111 by vacuum evaporation or other suitable method; the numeral 113 denotes an outer electrode layer of platinum deposited on the outer surface of the oxygen sensing element 111 like the inner electrode layer 112; the numeral 114 denotes an output withdrawing lead wire electrically connected to the inner electrode layer 112 for withdrawing the output of the inner electrode layer 112; the numeral 115 denotes a cylindrical housing for holding the oxygen sensing element 111, the housing 115 being electrically connected to the outer electrode layer 113; and the numeral 130 denotes a rod-like ceramic heater for heating the oxygen sensing element 111, the heater 130 being disposed in the interior of the oxygen sensing element 111, that is, in the inside bore defined by the inner electrode layer 112. The ceramic heater used herein is made by winding around a green aluminous core formed in an elongated tube shape a green aluminous sheet with a predetermined shape of a heater pattern of tungsten printed on one face and bringing the aluminous sheet into close contact with the aluminous core, then forming on the surface of one side thereof printed faces of tungsten serving as connecting terminal faces electrically connected to both ends of the above buried pattern via through holes, followed by burning and subsequent nickel plating applied to the exposed faces of tungsten. It is in the form of a tube having an outside diameter of about 2.5 mm and an overall length of about 60 mm. On the outer periphery of the housing 115 is formed a thread portion 115a for mounting the oxygen sensor to a combustion apparatus, and a gasket 116 for preventing the leak of exhaust gases is provided on the portion of the housing 115 to be brought into abutment with the wall surface of the combustion apparatus. The housing 115 is formed with a caulking portion 115b, and by caulking this caulking portion 115b the oxygen sensing element 111 is held by the housing 115 through plate packing 117, talc 118, caulking ring 119 and sleeve flange portion 122a, which are disposed on the inner periphery of the housing 115. The numeral 120 denotes a protector for protecting the oxygen sensing element 111. The protector 120, which is attached to a combustion apparatus-side fore end portion 115c of the housing 115, has a plurality of exhaust gas passing holes 120a so that exhaust gases may be brought into contact with the outer electrode layer 113.

The numerals 140 and 141 denote heater lead wires for supplying power to a heater 130. The heater lead wires 140 and 141 are connected to terminal faces of the heater 130 through heater terminals 140 and 141, respectively. As an example, the heater terminals 140 and 141 are connected to the heater lead wires by pressure bonding and connected to the heater terminal faces by soldering. The numeral 121 denotes a metallic terminal for connecting the inner electrode layer 112 of the oxygen detecting element 111 with the output withdrawing lead wire 114 and for holding the heater 130. The metallic terminal 121 has a connecting portion 121a formed by using a spring steel sheet which in this embodiment is stainless steel strip for spring SUS631-CSP, a precipitation hardening type stainless steel, and rounding it so as to exhibit a resilient force in a radial direction as will be described later, heater holding portions 121b also formed by rounding the same spring steel sheet for holding the ceramic heater inserted therethrough by virtue of their resilience, and a terminal portion 121b capable of being connected to the core of the output withdrawing lead wire 114 preferably by pressure bonding as shown in later-described FIG. 7 though not shown in FIG. 6. The connecting portion 121a is inserted under application of a compressive force into an inlet opening portion having a somewhat expanded inside diameter of the oxygen sensing element and then released whereby it is fixed in pressure contact and electrical connection with the inner electrode layer 112 formed on the inner surface of the opening and holds the ceramic heater in a predetermined position. Though not shown in FIG. 6, the core of the output withdrawing lead wire 114 is connected by pressure bonding to the terminal portion 121d of the metallic terminal. The numeral 122 denotes a tubular shell extending from the caulking portion of the housing and the metallic terminal of the ceramic heater, and the numeral 125 denotes a protective sleeve fitted and fixed onto the tubular shell. In the portion between an inwardly bent edge of the protective sleeve and a like edge of the tubular shell the protective sleeve 125 holds a spacer 123 and a seal member 124 with the lead wires 140, 141 and 114 inserted therethrough, and at the same time protects the heater -lead wire connection and the metallic terminal -lead wire connection.

Figure 7:
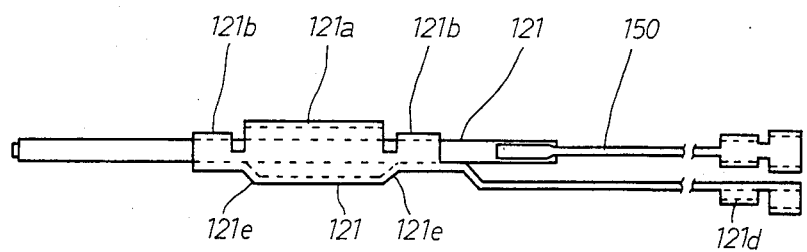
FIG. 7 illustrates a shape of a metallic terminal 15 used in the oxygen sensor of the second embodiment, in which A is a side view and B is a development view.
Figure 7:
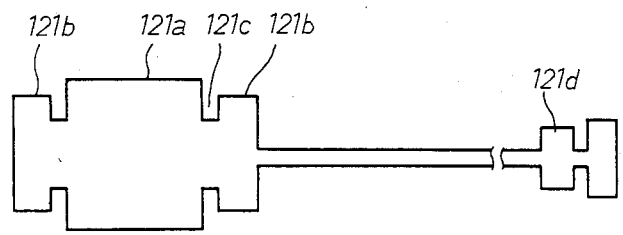

The metallic terminal 121, which is a principal portion of this embodiment, has such a shape as shown in FIG. 7. As is apparent from the development view B in FIG. 7, a metallic sheet is punched so as to form the connecting portion 121a centrally, two holding portions 121b provided on both sides of the connecting portion 121a through notches 121c, and the terminal portion 121d at an elongated end portion extending from one holding portion 121b. Then, the connecting portion 121a is round in the form of a cylinder having an inside diameter larger than that of an opening portion 111a of the oxygen sensing element, and the holding portions 121b are also round in the form of a cylinder having an inside diameter smaller than the outside diameter of the heater. In this case, bent portions 121e are formed so that the rounded connecting portion 121a and holding portions 121b are aligned with each other. The heater 130 is inserted through the heater holding portions 121b whereby it is held firmly by the metallic terminal 121, and by inserting the connecting portion 121a into the oxygen sensing element 111, the heater is fixed in the interior of the oxygen sensing element. The connecting portion 121a is fixed in the opening portion 111a while exhibiting a resilient force which urges the inner electrode layer 112 in the opening portion 111a in a radial direction, whereby the output of the inner electrode layer 112 can be surely taken out without being influenced by vibration or heat and at the same time the heater can be held in place. Thus, it is not necessary to form a thread portion in the interior of the oxygen sensing element 111, and the mounting operation can be done easily.

Figure 8:
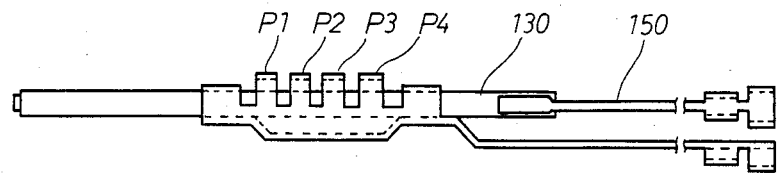
FIGS. 8 and 9 illustrate other examples or metallic terminals in which, like FIG. 7, A is a side view and B is a development view
Figure 8:
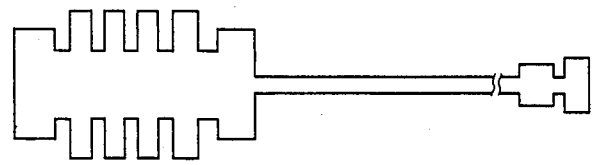
Figure 9:
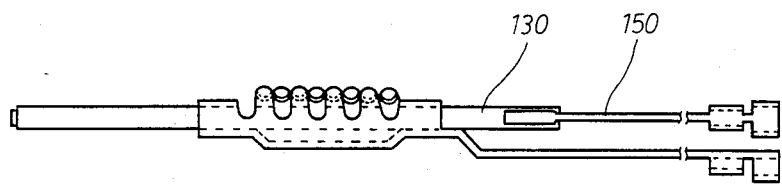
Figure 9:
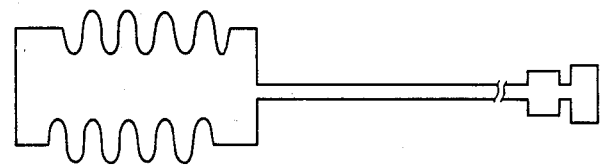

Although in this embodiment the metallic terminal 121 is formed by merely rounding a rectangular metallic sheet cylindrically, it may be obtained by forming rectangular notches in a metallic sheet and then rounding the sheet cylindrically as shown in FIG. 8, or by forming wavy notches in a metallic sheet and then rounding the sheet cylindrically as shown in FIG. 9. In this case, the metallic terminal has a plurality of pressing portions against the inner electrode layer. Therefore, for example, even in the event the metallic terminal is partially deformed by an external force and a pressing portion P1 shown in FIG. 8 loses its resilience, the metallic terminal can be firmly fixed to the inner electrode layer by the resilience of other pressing portions P2 to P4. Consequently, the heater can be fixed more firmly to the inside of the oxygen sensing element, and the output withdrawal from the inner electrode layer is ensured.

Moreover, above-mentioned embodiment can be equipped with a narrow and long gap between a tubular shell (22, 122) wherein a protective sleeve (25, 125), and the internal space of oxygen sensing element (11, 111) is connected to the external atmosphere through the narrow and long gap, preventing the water from entering, the Figure is omitted.

The above embodiments describe the invention in terms seem to be limited to the one of a construction fixing a protective sleeve (25, 125) to a tubular shell 22, 122. But, for example, it is also possible to fix the protective sleeve 25, 125 directly to housing 15, 115, as a matter of course.

What is claimed is:

1. An oxygen sensor comprising:
   a cylindrical oxygen sensing element having one closed end and inner and outer electrode layers formed on the inner and outer surfaces thereof respectively;
   an output withdrawing lead wire electrically connected to the inner electrode layer of the oxygen sensing element; and
   a metallic terminal disposed in the connection between the output withdrawing lead wire and the inner electrode layer, said metallic terminal having a connection portion formed of a rounded spring steel sheet with a larger uncompressed diameter than the inner diameter of said inner electrode layer and having opposed resilient portions separated by a gap and disposed in contact with an inner periphery of said inner electrode layer to apply a radial force to said inner electrode layer.

2. An oxygen sensor according to claim 1, wherein the oxygen sensing element (11) is maintained at a predetermined temperature by means of a heater, and the output withdrawing lead wire (14) and the inner electrode layer (12) are connected through a metallic terminal (21) which is adapted to be fixed in pressure contact with the inner periphery of the inner electrode layer (12) and which holds the heater (36).

3. An oxygen sensor according to claim 1, wherein said steel sheet has a diameter of 0.10–1.60 mm.

4. An oxygen sensor according to claim 1, wherein said steel sheet is SUS 631-CSP.

5. An oxygen sensor according to claim 1, wherein said steel sheet is Inconel X 750 alloy.

6. An oxygen sensor comprising:
   (a) an oxygen sensing element having one electrolyte;
   (b) an inner electrode layer formed of platinum on the inner surface of the oxygen sensing element;
   (c) an outer electrode layer formed of platinum on the outer surface of the oxygen sensing element;
   (d) an outer withdrawing lead wire electrically connected to the inner electrode layer for withdrawing the output of the latter; and
   (e) a metallic terminal for connecting the inner electrode layer of the oxygen sensing element with the output withdrawing lead wire,
   said metallic terminal having a connecting portion formed of a rounded spring steel sheet with a larger uncompressed diameter than the inner diameter of said inner electrode layer and having opposed resilient portions separated by a gap, the connection portion being inserted under application of a compressive force into an opening of the oxygen sensing element and then released from the compressive force so as to be fixed in resilient radial pressure contact and electrical connection with the inner electrode layer formed on the inner surface of the opening of the oxygen sensing element.

7. An oxygen sensor according to claim 6, further including a cylindrical housing (15) for holding the oxygen sensing element (11), the housing (15) being electrically connected to the outer electrode layer (13), and a protector (20) attached to a combustion apparatus-side fore end portion (15c) of the housing (15) for protecting the oxygen sensing element (11), the protector (20) having a plurality of exhaust gas passing holes (20a) for allowing exhaust gases to come into contact with the outer electrode layer (13).

8. An oxygen sensor according to claim 7, wherein the housing (15) has a thread portion (15a) formed on the outer periphery thereof for mounting the oxygen sensor to a combustion apparatus and a caulking portion (15b), and a gasket (16) for preventing the leak of exhaust gasses is provided on the portion of the housing (15) to be brought into abutment with the wall surface of the combustion apparatus, and by caulking the caulking portion (15b) the oxygen sensing element (11) is held by the housing (15) through plate packing (17), talc (18), caulking ring (19) and outer tubular shell flange portion (22a) which are disposed on the inner periphery of the housing (15).

9. An oxygen sensor according to claim 6, wherein the metallic terminal (21) and the output withdrawing lead wire (14) are connected by pressure bonding at a terminal portion (21b) and core (14a), and are protected by a protective sleeve (25) which is co-axially fixed directly or undirectly to a cylindrical housing for holding the oxygen sensing element, the protective sleeve (25) having a seal member (24) with the lead wire (14) being inserted therethrough, the seal member (24) being fixed to an end portion of the protective sleeve (25).

10. An oxygen sensor according to claim 9, wherein the metallic terminal (21) is formed by punching a metallic plate and has a connecting portion (21a) and a terminal portion (21b) provided at an end of an elongated extension extending from the connecting portion (21a), the connecting portion (21a) being formed cylindrically by rounding a metallic sheet.

11. An oxygen sensor according to claim 6, wherein the metallic terminal (21) is obtained by forming a rounded notch in a nearly rectangular metallic sheet and then rounding the metallic sheet cylindrically.

12. An oxygen sensor according to claim 6, wherein the metallic terminal (21) is obtained by forming a rectangular notch in a nearly rectangular metallic sheet and then rounding the metallic sheet cylindrically.

13. An oxygen sensor according to claim 6, wherein said steel sheet has a diameter of 0.10–1.60 mm.

14. An oxygen sensor according to claim 6, wherein said steel sheet is SUS 631-CSP.

15. An oxygen sensor according to claim 6, wherein said steel sheet is Inconel X 750 alloy.

16. An oxygen sensor comprising:
 (a) an oxygen sensing element having one closed end and cylindrically formed of a solid electrolyte;
 (b) an inner electrode layer formed of platinum on the inner surface of the oxygen sensing element;
 (c) an outer electrode layer formed of platinum on the outer surface of the oxygen sensing element;
 (d) an output withdrawing lead wire electrically connected to the inner electrode layer for withdrawing the output of the latter;
 (e) a metallic terminal for connecting the inner electrode layer of the oxygen sensing element with the output withdrawing lead wire; and
 (f) a rod-like ceramic heater for heating the oxygen sensing element, the ceramic heater being disposed in the interior of the oxygen sensing element;
 said metallic terminal having a connecting portion formed of a rounded spring steel sheet with a larger uncompressed diameter than the inner diameter of said inner electrode layer and having opposed resilient portions separated by a gap, a heater holding portion also formed of a rounded spring steel sheet to resiliently hold the ceramic heater which is inserted therethrough, and a terminal portion capable of being connected to the core of the output withdrawing lead wire by pressure bonding or by soldering, said connecting portion disposed into an inlet opening of said oxygen sensing element with said opposed resilient portions thereof in resilient radial pressure contact with said inner electrode layer.

17. An oxygen sensor according to claim 16, wherein the ceramic heater (130) is tubular and is made by winding around a green ceramic core formed in an elongated tube shape a green ceramic sheet with a predetermined shape of a heater pattern of a metal having high melting point printed on one face and bringing the ceramic sheet into close contact with the ceramic core, then forming on the surface of one side thereof printed faces of said metal serving as connecting terminal faces electrically connected to both ends of the buried pattern followed by burning.

18. An oxygen sensor according to claim 17, wherein said metal comprising at least one ingredient selected from the group consisting of platinum, tungsten and molybdenum.

19. An oxygen sensor according to claim 16, further including heater lead wires 140, 141 respectively connected by pressure bonding or by soldering to heater terminals (140, 141) which are connected by soldering to terminal faces of the heater (130).

20. An oxygen sensor according to claim 19, further including a tubular shell (122) extending from and fixed to a housing for holding the oxygen sensing element, and a protective sleeve (125) fitted and fixed onto the tubular shell (122), whereby a seal member (124) with leads (140, 141, 114) inserted therethrough are held in the portion between an inwardly bent edge of the protective sleeve (125) and a like edge of the tubular shell (125), and at the same time the heater-lead wire connection and the metallic terminal - lead wire connection are protected.

21. An oxygen sensor according to claim 19, further including a protective sleeve (125) coaxially fixed directly or indirectly to a cylindrical housing for holding the oxygen sensing element, said protective sleeve having a seal member (124), the seal member being fixed to an end portion of the protective sleeve (125).

22. An oxygen sensor according to claim 16, wherein the connecting portion is inserted into said inlet opening of the oxygen sensing element under application of a compressive force and while holding the heater and then released from said compressive force whereby the connecting portion is fixed in said resilient pressure contact with the inner electrode layer formed on the inner surface of said inlet opening portion to thereby hold said ceramic heater in a predetermined position and at the same time electrically connected to the inner electrode layer, and the core of the output withdrawing lead wire is connected to the terminal portion of the metallic terminal by pressure bonding or by soldering.

23. An oxygen sensor according to claim 16, wherein the metallic terminal (121) is obtained by punching a metallic sheet so as to form the connecting portion (121a) centrally, two holding portions (121b) formed on both sides of the connecting portion (121a) through notches (121c) and the terminal portion (121b) at an elongated end extending from one holding portion (121b), the connecting portion (121a) being round in the form of a cylinder having an inside diameter larger than that of an opening portion (111a) of the oxygen sensing element, the holding portions (121b) being round in the form of a cylinder having an inside diameter smaller than the outside diameter of the heater, the thus-rounded connecting portion (121a) and holding portions (121b) being aligned with each other by forming bent portions (121e), the heater (130) being inserted through the heater holding portions (121b) and thereby held by the metallic terminal (121) and further fixed in the interior of the oxygen sensing element (111) by inserting the connecting portion (121a) into the oxygen sensing element.

24. An oxygen sensor according to claim 16, wherein said steel sheet has a diameter of 0.10–1.60 mm.

25. An oxygen sensor according to claim 16, wherein said steel sheet is SUS 631-CSP.

26. An oxygen sensor according to claim 16, wherein said steel sheet is Inconel X 750 alloy.

* * * * *